United States Patent

Gazerro et al.

[11] Patent Number: 5,219,988
[45] Date of Patent: Jun. 15, 1993

[54] NEW GEM-DIAMINO DERIVATIVES AND THEIR USE IN THE SYNTHESIS OF RETRO-INVERSO PEPTIDES

[75] Inventors: Laura Gazerro, Merate; Massimo Pinori, Paderno D'Adda, Italy; Antonio S. Verdini, Monterotondo, all of Italy

[73] Assignees: Eniricerche S.p.A., Milan; Sclavo S.p.A., Siena, both of Italy

[21] Appl. No.: 482,653

[22] Filed: Feb. 21, 1990

[30] Foreign Application Priority Data

Feb. 22, 1989 [IT] Italy ............... 19518 A/89

[51] Int. Cl.$^5$ .............. A61K 37/02; C07K 5/00; C07K 7/00; C07C 233/00
[52] U.S. Cl. .................. 530/330; 530/331; 530/334; 548/495; 564/166; 564/199; 564/200; 564/209
[58] Field of Search ............... 530/334, 335, 336, 330, 530/331, 332, 329; 514/17, 18; 546/286; 548/495; 564/166, 199, 200, 209

[56] References Cited

U.S. PATENT DOCUMENTS

| | | | |
|---|---|---|---|
| 4,439,360 | 3/1984 | Verdini et al. | 260/112.5 R |
| 4,611,002 | 9/1986 | Ondetti | 514/419 |
| 4,638,046 | 1/1987 | Verdini et al. | 530/332 |
| 4,851,387 | 7/1989 | Koike et al. | 514/17 |
| 4,888,427 | 12/1989 | Bodor | 546/316 |

FOREIGN PATENT DOCUMENTS 0084691 8/1983 European Pat. Off. .

*Primary Examiner*—Lester L. Lee
*Assistant Examiner*—A. M. Davenport
*Attorney, Agent, or Firm*—Shea & Gould

[57] ABSTRACT

This invention relates to new gem-diamino derivatives of general formula (I)

$$X-NH-CH(R)-NH_2 \qquad (I)$$

where
R is the side chain of an amino acid, of which any functional groups are suitably protected, and
X is an acyl group chosen from the group consisting of 2-nitrobenzoyl, 4-chloro-butyryl, acetoacetyl, 4-bromo-butyryl, (2-nitrophenoxy)-acetyl and 2-methyl-2-(2'-nitro-phenoxy)propionyl, of use in introducing gem-diamino residues into retro-inverso peptides. The invention further relates to a method for the synthesis of retro-inverso peptides in which the gem-diamino residue or residues are introduced using the new compound (I).

11 Claims, No Drawings

NEW GEM-DIAMINO DERIVATIVES AND THEIR USE IN THE SYNTHESIS OF RETRO-INVERSO PEPTIDES

This invention relates to new gem-diamino derivatives of general formula (I)

$$X-NH-CH(R)-NH_2 \quad (I)$$

where

R is a side chain of an amino acid, of which any functional groups are suitably protected, and X is an acyl group chosen from the group consisting of 2-nitrobenzoyl, 4-chloro-butyryl, acetoacetyl, 4-bromo-butyryl, (2-nitrophenoxy)-acetyl and 2-methyl-2-(2'-nitro-phenoxy)propionyl, of use in introducing gem-diamino residues into retro-inverso peptides, and the method for the synthesis of retro-inverso peptides in which the gem-diamino residue or residues are introduced using the new compound (I).

Retro-inverso peptides are pseudo-peptides characterised by the inversion of the direction of one or more amide bonds of the amino acid sequence.

These pseudo-peptides, which maintain a side-chain topology similar to that of the corresponding natural peptide, often have the same biological activity as the unmodified molecule, whereas they are less susceptible to the degradative action of plasmatic peptidase and thus have a more lasting in vivo activity [see P. V. Pallai et al., Int. J. Peptide Protein Res., 21, pp. 84–92 (1983); M. Chorev et al., J. Med. Chem. 26, pp. 129–35, (1983); M. Pinori et al., in "Peptide Chemistry"-Shiba & Sakakibara Eds., pp. 645–48, Protein Research Foundation-Osaka (1987); N. Chaturvedi et al., Int. J. Peptide Protein Res., 17, pp. 72–78 (1981); M. Chorev et al., Science, vol. 204, pp. 1210–12 (1979); Chem. Abstr. 101, 231005a; Chem. Abstr. 102, 160548 n, 185470u, and 221202u]. In particular, the inversion of the direction of a peptide bond, from a partial structure (a)

$$\sim\sim NH-CH(R)-CO-NH-CH(R')-CO\sim \quad (a)$$

to a partial structure (b)

$$\sim\sim NH-CH(R)-NH-CO-CH(R')-CO\sim \quad (b)$$

can be effected, without altering the position of the terminal amino and carboxyl groups, by inserting into the peptide sequence a 2-substituted malonic acid residue (c)

$$\sim\sim CO-CH(R')-CO\sim\sim \quad (c)$$

and a gem-diamino residue (d)

$$\sim\sim NH-CH(R)-NH\sim\sim \quad (d)$$

[see M. Goodman and M. Chorev, Acct. Chem. Res., vol. 12, p. 17 (1979)].

The preparation of gem-diamino residues and their insertion into the pseudo-peptide chains is very difficult, substantially due to the instability of such gem-diamino derivatives, which tend to hydrolyze spontaneously to produce ammonia and the corresponding aldehyde. In practice, such gem-diamino derivatives can be prepared from the corresponding N-acyl-amino acids by converting the carboxyl group into an amino group by one of the various rearrangement methods well known in organic chemistry (Curtius, Lossen, Hoffman), or more simply by starting from the primary amide of the amino acid and converting the carboxyamido group into a primary amino group using the oxidizing reagent I,I[-bis(trifluoroacetoxy)]iodobenzene (TIB) [see A. Pessi et al., J. Chem. Soc. Chem. Commun., p. 195 (1983)]. Thus by using as the protecting group for the amino function a conventional protective group of urethane type (Boc, Z, Fmoc) or not (TFA, Nps, Dpp etc.), the monoacyl diamine thus obtained is too unstable for convenient use in peptide synthesis (P. V. Pallai et al., op.cit).

The mono-peptidyl- and mono-malonyl-diamines have proved relatively more stable, so that the strategy currently followed for introducing a gem-diamino residue into a pseudo-peptide chain comprises constructing peptide or pseudo-peptide fragments containing the primary amide of the amino acid to transform, followed by rearranging this into the gem-diamine using TIB. This strategy in its possible (A) and (B) variations is described in the following Scheme I

SCHEME I (L)      (A)

$$P\ldots AA_{n-1}-NH-CH(R)-CONH_2$$
$$\downarrow TIB$$
$$P\ldots AA_{n-1}-NH-CH(R)-NH_3^{\oplus}TFA^{\ominus}$$

(where P is a protecting group for the terminal amino acid group)

(B)

$$\begin{array}{l} CH(R')-CO-AA_{n+2}\ldots P' \\ | \\ CO-NH-CH(R)-CONH_2 \end{array}$$

(D) $\downarrow$ TIB $$TFA^{\ominus\oplus}H_3N-CH(R)-NH-CO-CH(R')-CO-AA_{n+2}\ldots P'$$

(where P' is a protecting group for the terminal carboxyl). It is apparent that in variant (B), the side-chain of the residue is in a configuration topologically similar to that of an amino acid of configuration opposite to that of the starting amide; equally, if more than one adjacent bonds are to be retro-inverted, other amino acid residues of opposite configuration to that of the natural sequence must be inserted between the malonyl residue and the diamino residue.

The main limit to this strategy is the need to expose other amino acid or malonyl residues to the oxidizing action of TIB. The limit is even more critical in solid-phase synthesis because in this case the usual method implies the use of variant (B), making the exposure of the terminal carboxy segment of the peptide to the action of TIB inevitable.

It has now been found, and represents a first aspect of the present invention, that it is possible to sequentially introduce a gem-diamino residue into a peptide or pseudo-peptide chain by using a suitable mono-acylated gem-diamino derivative of general formula (I)

$$X-NH-CH(R)-NH_2 \quad (I)$$

where

R is the side chain of the amino acid to be introduced as the gem-diamino residue, and of which any functional groups are suitably protected, and X is an acyl radical chosen from the group consisting of 2-nitro-benzoyl, 4-chloro-butyryl, acetoacetyl, 4-bromo-butyryl, (2-nitro-phenoxy)-acetyl and 2-methyl-2-(2'-nitro-phenoxy)propionyl. The mono-acylated gem-diamino derivatives of formula (I) are stable compounds, both in salified form and as free bases; they react favourably under suitable conditions with amino acids or with partially protected malonic acid derivatives or with peptide or pseudo-peptide fragments constructing pseudo-peptide chains; the acyl group X can be easily removed by known methods which do not expose the gem-diamino residue to excessively basic conditions (pH>8) and/or to high temperature for prolonged periods; and finally they can be easily synthesized from the corresponding N-acyl-amino acids (II)

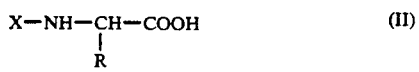

where X and R have the aforesaid meaning, or from the corresponding methyl esters, by converting these to the carboxyamides (III)

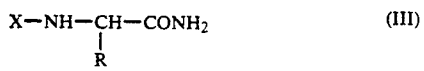

and treating these latter with TIB by conventional methods. More specifically, the carboxyamides (III) can be easily prepared from the methyl esters of N-acyl-amino acids by treatment with an alcoholic solution saturated with ammonia; alternatively they can be obtained by reacting N-acyl-amino acids with the ammonium salt of 1-hydroxy-benzotriazole in the presence of dicyclohexylcarbodiimide.

With regard to the conversion of carboxyamides (III) to amines I by the use of TIB, the reaction conditions already described for example by A. Pessi et al., in J. Chem. Soc. Chem. Commun., p. 195 (1983) or by P. V. Pallai et al., in Int. J. Peptide Protein Res., 21, pp. 84–92 (1983) can well be used to obtain the gem-diamino derivatives (I).

It is however possible, if desired, to synthesize the gem-diamino derivatives (I) by other known methods such as those described by M. Chorev and M. Goodman in Int. J. Peptide Protein Res., vol. 21, pp. 258–68 (1983).

The starting N-acyl-amino acid methyl esters (II), which in general are known products, can also be prepared by classical acylation methods. The N-acyl-amino acids (II) can be obtained from these esters by simple hydrolysis.

As anticipated, the compounds of formula (I) can be conveniently used in any peptide synthesis process (synthesis in solution or in solid phase, assembly stepwise or by fragments), by incorporating the corresponding gem-diamino residue into the desired pseudo-peptide sequence.

In this respect, the compounds of formula (I) can react, using the methods known in peptide synthesis such as the activated ester method, with di-cyclohexylcarbodiimide in the presence of 1-hydroxybenzotriazole, or the mixed anhydride method etc., with amino acids, partially protected malonyl derivatives, or peptide or pseudo-peptide fragments.

On termination of the condensation reaction, the protecting group X is removed, using methods known in the conventional synthesis field, under mild conditions which do not damage the peptide structure and which are typical for each particular protecting group.

In greater detail, when X represents the 2-nitro-benzoyl group, a classical removal method comprises reducing the nitro group to amino by hydrogenation, followed by treatment with copper salts [A. K. Koul et al., Tetrahedron, 29, pp. 625-28 (1973)]

In contrast, when X represents a 4-chloro or 4-bromo-butyryl group, the chosen deprotection method comprises treatment with silver perchlorate in acetone or acetone/water [see H. Peter et al., Helvetica Chimica Acta, vol. XLVI, pp. 577–86 (1963)].

Again, the acetoacetyl group is easily removed by adding an equimolar quantity of an arylhydrazine, typically phenylhydrazine, to a solution of the retro-inverso peptide or a fragment thereof containing the thus protected gem-diamino residue, in acetic acid [see F. D'Angeli et al., Tetrahedron Letters, No. 10, pp. 605–8, (1965)].

The (2-nitro-phenoxy)acetyl group can be removed either by hydrogenation with hydrogen and palladium or by treatment with KBH$_4$ in the presence of palladium on carbon. Finally, when according to a preferred aspect of the present invention the 2-methyl-2-(2'-nitro-phenoxy)propionyl group (IV)

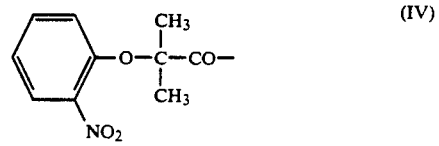

is used as the protecting group X, this can be generally removed, in the case of synthesis in solution, by treatment with triethylsilane in the presence of palladium sponge, and in the case of solid phase synthesis by treatment with a large excess of a solution of stannous chloride in dimethylformamide. The protecting groups for those functions present in the side chain, both for the reaction partner of the gem-diamino derivative and of the derivative itself, are suitably chosen according to the protecting group X to be used, the chosen removal method and the synthesis strategy to be followed.

In particular, if for example the group of formula (IV) is used as the protecting group X, independently of the removal method to be followed it is possible to use the conventional acid-labile protecting groups for side-chain protection (typically tertiary alkyl esters or ethers), and if the stannous chloride removal method is used this does not interfere with the protections of benzyl type, these being removed by catalytic hydrogenation. The compounds of formula (I) can alternatively be reacted, in accordance with the method described in the European patent application N. 0375040, with cyclic esters of 2-substituted malonic acids, the so-called Meldrum acids of general formula (V)

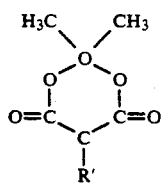

(V)

where

R' is the side chain of any amino acid, any functional groups of which are protected, in the presence of an at least equimolar quantity of a silylating agent chosen from tri-alkyl-silyl halides and N,O-bis-tri-alkyl-silyl-acetamides.

On termination of the condensation reaction, a mild acid hydrolysis removes the trialkylsilyl group, the protecting group X being removed by the methods indicated heretofore. For the purposes of the present invention, a preferred group of compounds of formula (I) comprises those compounds in which R represents the possibly protected side chain of the amino acids glycine, alanine, valine, leucine, isoleucine (useful for preparing the retro-inverso peptide analogues of neurotensin described in EP-A-215410), threonine (useful in the synthesis of a retro-inverso analogue of tuftsin described in EP-A-253190) arginine, aspartic acid (useful in the preparation of the bi-retro-inverso analogue of thymopentin described in the European patent application N. 0375058), phenylalanine [useful in the preparation of the retro-inverso analogues of encephalinamides described in Science, 204, p.1210-2 (1979)], tyrosine, proline [useful in preparing the retro-inverso analogues of LH-RH described in Int. J. Peptide Protein Res., 17, pp.72-88 (1981)], tryptophan [useful in the preparation of the retro-inverso analogue of somatistatin described in Biochemistry, 24 (8), pp.1933-41, (1985)], and lysine [useful in the preparation of a retro-inverso analogue of $BPP_{9a}$ described in Int. J. Peptide Protein Res., 24 (6), pp.553-6 (1984)].

A still more preferred group of compounds of formula (I) are those compounds in which R has the aforesaid meaning and X is a 2-methyl-2-(2'-nitro-phenoxy)-propionyl group.

The following examples, which illustrate some compounds representative of formula (I), their preparation and their use in the synthesis of pseudo-peptide sequences, must not be interpreted as limitative of the scope of the invention.

Condensation of a compound of formula (V) with the suitably selected N-trialkyl-silyl derivative, readily affords effective acylation of the amino group.

An additional advantage deriving from the use of this method to incorporate the malonyl residue, resides in the possibility, by simple hydrolysis of the obtained product at neutral or slightly acidic pH, of setting free the carboxyl group of the pseudo-peptide terminal malonyl residue, which is then available for the formation of the next amide group.

In the actual practice, condensation between Meldrum's acid derivative (V) and the suitably selected N-tri-alkyl-silyl derivative, is carried out by contacting a compound of formula (V) wherein R' is as defined above, with at least an equimolar amount, and preferably a slight excess, of the N-tri-alkyl-silylated reaction partner.

The two reactants are contacted in the presence of an inert inorganic solvent. In general, polar, aprotic, organic solvents such as, for instance, halogenated aliphatic or aromatic hydrocarbons, e.g. methylene chloride, dichloroethane, chloroform, chlorobenzene, etc., cyclic or linear ethers, e.g. tetrahydrofuran, dioxane, diethyl ether, etc., and etherated glycols, e.g. ethylene glycol mono-methyl or mono-ethyl ether, can conveniently be employed.

Condensation is typically carried out at a temperature of from 0° C. to the reflux temperature of the reaction mixture and, preferably, at a temperature of from 15° to 50° C.

EXAMPLE 1

2-methyl-2-(2'-nitro-phenoxy)propionyl-phenylalanyl-amide ($MNP-Phe-NH_2$)

2-methyl-2-(2'-nitrophenoxy)propionyl-phenylalanine methyl ester (MNP-Phe-OMe) (14 g; 36.2 mmoles) is dissolved under stirring at ambient temperature in a saturated solution of ammonia in methanol (150 ml). After 2 days the ammonia is evaporated, the mixture evaporated to dryness and the residue is triturated with ethyl ether.

It is then recrystallized from $MeOH/Et_2O$ to obtain 10.67 g (equivalent to 80% of theoretical) of the compound of the title, with a M.P. of 138°–39° C.

The identity of the product is confirmed by IR, $^1H$-NMR and FAB-mass analysis.

The homogeneity of the product is confirmed by HPLC under the following experimental conditions:

Column: Hibar RP-18 (10µ, 25×0.4 cm);
Detector: Jasco-UV 254 and 230 nm;
Solution A: 90% $H_2O$, 10% MeCN, 0.1% TFA
Solution B: MeCN, 0.1% TFA
Gradient from 0 to 40% B (20 min) and 80% B (10 min)
Retention time ($t_R$): 21.69 min.

EXAMPLE 2

1-[2-methyl-2-(2'-nitrophenoxy)propionylamino]-1-amino-2-phenylethane hydrochloride
[MNP-(g)Phe.HCl]

The compound of Example 1 (2 g; 5.4 mmoles) is added, under stirring at ambient temperature, to a $MeCH/H_2O$ solution (1/1 v/v, 70 ml) containing TIB (2.4 g; 5.4 mmoles).

After 4 hours the acetonitrile is removed, the mixture is acidified with 0.1N HCl (5.4 ml), evaporated to dryness, and the residue triturated with a small quantity of $Et_2O$ to obtain 1.97 g (98.5%) of the compound of the title.

M.P. 132° C. (dec.).

The product structure is confirmed by $^1H$-NMR and FAB-mass analysis.

HPLC analysis under the conditions described in example 1 gives a single peak with $t_R$ 18.49 min.

EXAMPLE 3

2-methyl-2-(2'-nitrophenoxy)propionyl-alanylamide ($MNP-Ala-NH_2$)

2-methyl-2-(2'-nitrophenoxy)propionyl-alanine methyl ester (MNP-Ala-OMe) (1.65 g; 5.4 mmoles) is dissolved under stirring at ambient temperature in a saturated solution of $NH_3$ in methanol (20 ml). After 2 days the $NH_3$ is evaporated, the mixture evaporated to dryness and the residue triturated with $Et_2O$ to obtain 1.42 g (94%) of the compound of the title.

M.P. 95°-96° C.

The product structure is confirmed by IR, $^1$H-NMR and FAB-mass analysis.

HPLC (under the conditions described in Example 1) $t_R$ 14.23 min.

EXAMPLE 4

1-[2-methyl-2-(2'-nitrophenoxy)propionylamino]-1-amino-ethane hydrochloride [MNP-(g)Ala.HCl]

The compound of Example 3 (1 g; 3.4 mmoles) is added, while stirring at ambient temperature, to a MeCN/H$_2$O solution (1/1 v/v, 20 ml) containing TIB (1.46 g; 3.4 mmoles).

After 5 hours the acetonitrile is evaporated, the mixture is acidified with 0.1N HCl (3.4 ml), evaporated to dryness, and the residue triturated with a small quantity of Et$_2$O to obtain 0.98 g (95%) of the compound of the title.

M.P. 133° C. (dec.).

The product structure is confirmed by IR, $^1$H-NMR and FAB-mass analysis.

HPLC analysis under the conditions described in Example 1 gave a single peak with $t_R$ 11.70 min.

EXAMPLE 5

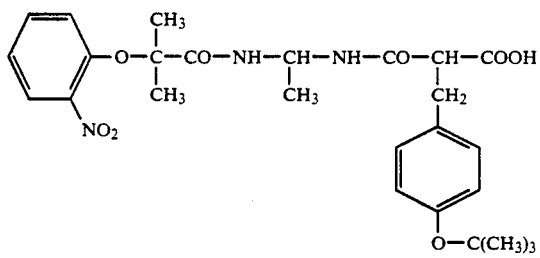

[MNP-(g)Ala-(m)Tyr($^t$Bu)-OH]

The compound of Example 4 (1 g; 3.3 mmoles) and 5-[(4-t-butoxyphenyl)methyl]-2,2-dimethyl-1,3-dioxane-4,6-dione [(M)Tyr($^t$Bu)] (1 g; 3.3 moles) are dissolved in tetrahydrofuran (100 ml) while stirring at ambient temperature.

N,O-bis-trimethylsilylacetamide (BSA) (2.42 ml, 9.85 mmoles) is slowly added to the solution obtained. After 10 hours the reaction mixture is evaporated to dryness, the residue taken up in H$_2$O and acidified with 0.1N HCl (pH 3) in the presence of AcOEt. It is then extracted twice with AcOEt, the organic phase dried and then evaporated to dryness.

The product of the title is obtained (1.65 g, 97%) by precipitation from Et$_2$O with hexane.

M.P. 87°-89° C.

The product structure is confirmed by $^1$H-NMR and FAB-mass analysis.

HPLC (under the conditions described in Example 1) $t_R$ 24.77 min.

EXAMPLE 6

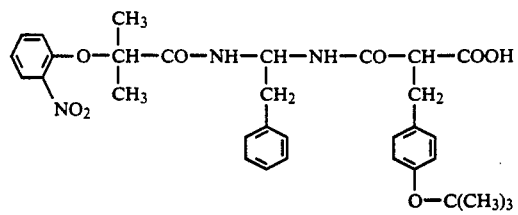

[MNP-(g)Phe-(m)Tyr($^t$Bu)-OH]

The compound of Example 2 (1.8 g; 4.8 mmoles) and (M)Tyr($^t$Bu) (1.47 g; 4.8 mmoles) are dissolved in tetrahydrofuran (70 ml) while stirring at ambient temperature.

BSA (3.52 ml, 14.4 mmoles) is slowly added to the solution obtained. After 10 hours the reaction mixture is evaporated to dryness, the residue taken up in H$_2$O and acidified with 0.1N HCl (pH 3.0) in the presence of AcOEt. It is then extracted twice with AcOEt, the organic phase dried and then evaporated to dryness.

The product of the title is obtained (2.8 g, 100%) by precipitation from Et$_2$O with hexane.

M.P. 61°-62° C.

The product structure is confirmed by $^1$H-NMR and FAB-mass analysis.

HPLC (under the conditions described in Example 1) $t_R$ 27.65 min.

EXAMPLE 7

1-[2-methyl-2-(2'-nitrophenoxy)propionylamino]-1-[Nα-fluorenylmethoxy-carbonyl-alanylamino]-2-phenyl-ethane [Fmoc-Ala[MNP-(g)Phe]]

Nα-fluorenylmethoxycarbonyl-alanine (0.9 g; 2.9 mmoles) is dissolved at ambient temperature under stirring in CH$_2$Cl$_2$ (20 ml), and a solution of 1-hydroxybenzotriazole (0.470 g; 3.45 mmoles) (HOBT) in DMF (1.5 ml) is added to the solution obtained. The reaction mixture is cooled to 0° C. and dicyclohexylcarbodiimide (DCC) (0.595 g; 2.9 mmoles) in CH$_2$Cl$_2$ (5 ml) is added. After 10 minutes it is filtered into a vessel containing the compound of Example 2 (1 g; 2.65 mmoles) and is neutralized with triethylamine (0.37 ml; 2.65 mmoles). The temperature is allowed to rise spontaneously to ambient by leaving overnight, after which the dicyclohexylurea (DCU) which forms is filtered off. The filtrate is evaporated to dryness and the residue taken up in AcOEt. The organic phase is treated with a 5% aqueous NaHCO$_3$, then with a 5% aqueous KHSO$_4$ solution, and is finally washed with water until neutral and then dried. The solvent is then removed by evaporation and the product (1.65 g; 98%) is precipitated by adding Et$_2$O.

M.P. 147°-48° C.

The product structure is confirmed by $^1$H-NMR and FAB-mass analysis.

HPLC (under the conditions described in Example 1) $t_R$ 29.93 min.

EXAMPLE 8

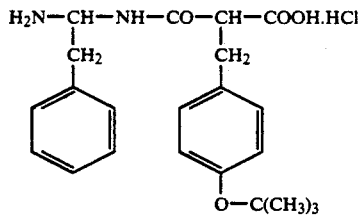

[H-(g)Phe-(m)Tyr(tBu)-OH.HCl]

The compound of Example 6 (1.2 g; 2.04 mmoles) is dissolved in methanol (2 ml) in the presence of Pd sponge, and triethyl silane (Et$_3$SiH) (5 ml) is added to the mixture. After 45 minutes the catalyst is filtered off, the reaction mixture evaporated to dryness, the residue taken up in CH$_2$Cl$_2$ and H$_2$O and acidified to pH 3.5 with 0.1N HCl. It is then extracted with CH$_2$Cl$_2$, the aqueous phase heated to evaporate solvent, and then lyophilized to obtain 0.730 g of the product of the title (85%). M.P. 70°–73° C. The product structure is confirmed by $^1$H-NMR and FAB-mass analysis.

HPLC (under the conditions described in Example 1): two peaks for the two diastereoisomers, with $t_R$ 18.05 and 19.26 min.

EXAMPLE 9

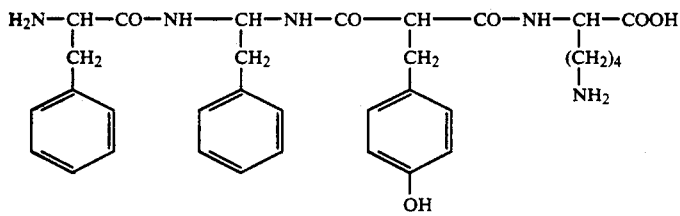

[H-Phe$^1$-(g)Phe$^2$-(m)Tyr$^3$-Lys$^4$OH]

To prepare the compound of the title the solid phase synthesis method is employed, using a polyamide resin having norleucine (Nle) as the internal reference amino acid and p-hydroxymethylphenoxy-acetic acid as handle. The nominal charge is 1 meq/g. The C-terminal lysine residue is condensed with 0.5 g of the thus modified resin.

The esterification reaction is conducted by introducing Fmoc-Lys(Boc)-OH (1 mmole), NMM (110 μl; 1 mmole) and DMAP (0.012 g; 0.1 mmole) into the reactor. The reaction is conducted under stirring at ambient temperature for 45 minutes. The mixture is then treated with piperidine/DMF (1/5 v/v) to remove the Fmoc N-protecting group, after which the compound of Example 6 (0.592 g; 1 mmole), DCC (0.206 g; 1 eq.) and HOBT (0.169 g; 1.25 eq.) dissolved in DMF are added. The acylation reaction is conducted under stirring at ambient temperature for 3 hours.

The MNP N-protecting group is removed by two successive treatments with a 2M solution of SnCl$_2$.2H$_2$O in DMF (8 ml), the first lasting for 15 minutes and the second for 45 minutes.

Ten washes with DMF (8 ml) are then carried out lasting one minute each, followed by three one-minute treatments with a solution of di-isopropylethylamine (DIPEA) in DMF (1/10 v/v) (8 ml). Finally, the resin is washed five times with DMF (8 ml).

The amino acid derivative (Boc-Phe)$_2$O is then condensed by the usual methods for solid phase synthesis. The thus synthesized tetrapeptide is cleaved from the resin and dried by treatment with conc. HCl (10 ml, 8 minutes, 0° C.). The desired peptide is then purified by ion exchange chromatography.

HPLC (under the conditions described in Example 1): two peaks for the two diastereoisomers, with $t_R$ 11.05 and 11.44 min.

EXAMPLE 10

Synthesis of retro-inverso analog of Tuftsin: H-gThr(R,S)mLys-Pro-Arg-OH 1) 2-methyl-2(2'-nitrophenoxy)propionyl-(O-tert-butyl)threoninamide (MNP-Thr(Bu$^t$)-NH$_2$)

MNP-OH(2.53 g, 11.26 mmoles) was dissolved in CH$_2$Cl$_2$ (20 ml), and DCCI (1.16 g, 5.63 mmoles) was added. The mixture was stirred for 5 min, then the formed DCU was filtered off, and the clear solution was added to 30 ml of CH$_2$Cl$_2$ containing L-Thr(Bu$^t$)-NH$_2$ (0.98 g, 5.63 mmoles) and N-methylmorfoline (NMM) (0.62 ml, 5.63 mmoles). The reaction mixture was stirred for 1 h at 22° C. The organic phase was then extracted with aqueous NaHCO$_3$ (5% w/v), citric acid (5% w/v), and water until the pH was neutral. The organic solution was dried over Na$_2$SO$_4$ and the solvent was removed in vacuo, yielding a colourless oil, corresponding to the desired product (according to the H-NMR and FAB-MS spectra), homogeneous by HPLC analysis. Yield: 88%.

2) 1[-2-methyl-2-(2'-nitrophenoxy)propionylamino-]1-amino-2-tertbutoxy-propane (MNP-gThr(Bu$^t$)

MNP-L-Thr(Bu$^t$)-NH (0.25 g, 0.65 mmoles was dissolved in a 2:1 (v/v) mixture acetonitrile (Accn) water buffered at pH=3.5 with CH$_3$COONH$_4$. A solution of TIB in AcCN (0.27 g, 0.65 mmoles) was slowly added, and the solution was stirred for 2 h at 22° C. The mixture was diluted with water, the organic solvent was removed in vacuo, and the aqueous phase was partitioned with diethyl ether, to eliminate the formed iodobenzene; the product was then recovered by freeze-drying. MNP-g-Thr(Bu$^t$) was purified by preparative RP-HPLC (230×20 mm) column, lichroprep RP-18 (25–40 μm), eluant AcCN/H$_2$O/TFA 35:64.9.01, flow 8 ml/min, detection UV 230 nm). The structure of the compound was confirmed by FAB-MS and $^1$H-NMR analysis. Yield after chromatography 64%.

3) 2,2-dimethyl-1,3-dioxane-5-(4-trifluoroacetamido-butyl)-4,6-dione [(M)Lys(TFA)]

4-amino-butyraldehyde diethylacetal (32.2 g, 200 mmoles) was dissolved in CH$_2$Cl$_2$ 600 ml), the solution was cooled to 0° C., and 4-dimethylaminopyridine (25.6 g, 210 mmoles) and, dropwise, tri-fluoroacetic anhydride (29.4 ml, 210 mmoles) in CH$_2$Cl$_2$ (100 ml) was added. After 30 min, the formed precipitate was filtered and washed with water. The organic phase was dried over Na$_2$SO$_4$, and the solvent was removed in vacuo, leaving an oily residue (48 g). 500 ml of 1N HCl were added in portions under vigorous stirring (22° C.), the addition being completed in 15 min. The pH was adjusted to 6 by 1N NaOH, and the solution was heated to 100° C. for 15 min, cooled to 22° C., and concentrated. The aqueous phase was extracted thrice with $CH_2Cl_2$, the organic solution was dried over $Na_2SO_4$, and the solvent was removed in vacuo yielding an oily product, homogeneous by TLC and HPLC (27 g). This product was added to 50 ml of DMF containing $NaBCH_3CN$ (3.3 g, 52 mmoles) and 2,2-dimethyl-dioxane-4,6-dione (Meldrum's acid, 12 g, 84 mmoles). After 1 h at 22° C., water was added (150 ml), and the pH was adjusted to 4.5, whereupon a precipitate formed, which was filtered off, washed with cold water, triturated with $Et_2O$, and dried in vacuo. The structure of the compound was confirmed by NMR and MS spectra; m.p.=131°-132° C.; elemental analysis: calculated for $C_{12}H_{16}O_5NF_3$, c=46.3, H=5.15, N=4.5; found, C=46.5, H=5.3, N=4.6. Yield: 17.5 g, 28% (calculated on the starting aldehyde).

4) (2,2-dimethyl-5-(4-tert-butoxycarbonylamino-butyl)-1,3-dioxane-4,6-dione) [(M)Lys(Boc)]

A solution of the compound obtained in step 3) [(M)Lys(TFA)] (6.22 g, 20 mmoles) in water (50 ml) is brought to pH 12.5 by the addition of 2N NaOH. The mixture is stirred at room temperature for 30 minutes and then cooled to 0° C. A solution of di-tert-butyl-carbonate (8.72 g, 40 mmoles) in dioxane (75 ml) is added thereto and the reaction mixture is allowed to warm up to room temperature and stirred for 2 h keeping the pH at 9. Dioxane is evaporated off under reduced pressure and the aqueous solution is washed with n-hexane. The pH is brought to 3.5 by the addition of citric acid and the solution is extracted few times with methylene chloride. The organic extracts are pooled, dried over $Na_2SO_4$ and evaporated to afford a white solid (5.4 g, 86%) with m.p. 112°-3° C.

$^1$H-NMR confirms the assigned structure.

5) [(2-R,S)-2-carboxy-6-(N-tertbutyloxyoxycarbonyl) amino]-hexanoyl-prolyl-($N^G$-nitro)-arginine benzyl ester [(R,S)mLys(Boc)ProArg($NO_2$)OBzl]

0.1 g (0,22 mmoles) of prolyl-($N^G$-nitro)arginine benzyl ester hydrochloride (HCl.ProArg($NO_2$)OBzl) was suspended in THF together with 1.1 equiv. (0.076 g, 0.24 mmoles) of (M)Lys(Boc); the mixture was cooled to 0° C. and a solution of BSA in THF (0.117 ml, 0.48 mmoles) was added dropwise; the solution was warmed to room temperature and TMSC (0.028 ml, 0.22 mmoles) was added. All the operations were carried out in nitrogen atmosfere to exclude moisture. After 3 h 1 more equiv. of TMSC was added, and the mixture was then stirred overnight. The mixture was diluted with 5% (p/v) $NaHCO_3$ and partitioned with EtOAc; the pH of the aqueous phase was adjusted to 3.5 and the mixture was again partitioned with EtOAc; the organic phase was washed with water to neutral pH, then dried over $MgSO_4$. The solvent was finally removed to yield a white foam (0.12 g, 81.8%). The compound analyzed as a single peak in RP-HPLC (conditions:eluant a, water (1% AcCN, 0.1% TFA); eluant b, AcCN (0.1% TFA); column, lichrosorb RP-18, 10 μm, 250×46 mm; flow, 1.5 ml/min; linear gradient, 10-70% b (10 min) then isocratic 70% b; detection, UV, 230 nm; t=11.21 min); the structure of the compound was confirmed by FAB-MS and NMR analysis.

6. [(2-R,S)-2-{N-[1-(N-(2-methyl-2-(2'-nitrophenoxy)propionyl)amino)-2-(oxytertbutyl)-propyl]-carbamyl}-6-(N-tertbutyloxycarbonyl)amino]-hexanoylpropyl($N^G$-nitro)arginine benzyl ester (MNP-gThr(Bu$^t$)(R,S)mLys(Boc)ProArg($NO_2$)OBzl)

(R,S)mLys(Boc)ProArg($NO_2$)OBzl (0.17 g, 0.256 mmoles) was dissolved in $CH_2Cl_2$ (3 ml, plus 3-4 drops of DMF), together with HOBt (0.035 g, 0.256 mmoles); the solution was cooled to 0° C. and DCC (0.053 g, 0.256 mmoles) was added as a solid; the mixture was stirred for 15 min at 0° C., then for 10 min at room temp., whereupon DCU precipitated; a solution of MNP-g-Thr(Bu$^t$) (0.11 g, 0.31 mmoles, in 2 ml of $CH_2Cl_2$) was then added, together with 32 ul (0.3 mmoles) of NMM; the mixture was then stirred overnight. After filtration of the DCU, the solvent was removed in vacuo, and the residue taken up in EtOAc; the organic phase was washed with 5% (p/v) NaHCO, water, 5% (p/v) citric acid, and water to neutral pH, then dried over $MgSO_4$. After removal of the solvent, a white solid foam was obtained. Yield: 0.2 g, 80%. The completely protected peptide analyzed as a single peak ($t_r$=18.31 min.) in RP-HPLC (linear gradient 10-70% b (15 min) then isocratic 70% b, other conditions as before) and the structure was confirmed by FAB-MS and NMR analysis.

7) H-gThr(Bu$^t$) (R,S)mLys(Boc)ProArg($NO_2$)OBzl

MNP-g-Thr(Bu$^t$) (R,S)mLysProArg($NO_2$)OBzl (0.2 g, 0.2 mmoles) was dissolved in DMF, and 5 equiv. of solid $SnCl_2$(0.225 g, 1.0 mmoles) were added; the solution was stirred overnight at room temp.; after removal of the solvent in vacuo, the residue was taken up in water and freeze-dried. Desalting of the desired compound was achieved by RP-HPLC according to T. F. Gabriel (int. J. Peptide Protein Res., (1987), 30, 40-43), the peptide was recovered by lyophylization. Yield: 98%.

8) H-gThr(Bu$^t$) (R,S)mLys(Boc)ProArg-OH

H-g-Thr(Bu$^t$) (R,S)mLys(Boc)ProArg($NO_2$)OBzl (0.052 g, 0.065 mmoles) was dissolved in MeOH, and 80 mg of Palladium Sponge, together with 0.042 g of $NH_4HCOO$ were added; the mixture was stirred for 2 h at 22° C. After filtering the catalyst off, the solvent was removed in vacuo, and the residue taken up in water (40 ml), and extracted twice with $Et_2O$; the organic phase was back-extracted with water, and the aqueous phases pooled and freeze dried. The structure of the desired peptide was confirmed by FAB-MS analysis. Yield: 0.033 g, 0.048 mmoles, 74%.

9) H-gThr(R,S)mLysProArg-OH

The lyophylized peptide from the preceeding reaction was dissolved in a saturated solution of HCl in EtOAc (20 ml), and the clear solution was stirred for 1 h at 22° C. The solvent was removed first by a Nitrogen stream, and then by rotary evaporation; the residue was dissolved in water and lyophylized three times to completely remove excess $NH_4HCOO$. The structure of the desired compound was confirmed by FAB-MS analysis. Yield: 0.02 g, 0.039 mmoles, 81%.

We claim:

1. A compound of formula (I)

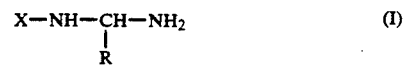

where

R is a side chain of an amino acid, of which any functional groups are suitably protected, and X is an acyl group chosen from the group consisting of 2-nitrobenzoyl, 4-chloro-butyryl, acetoacetyl, 4-bromo-butyryl, (2-nitrophenoxy)-acetyl and 2-methyl-2-(2'-nitro-phenoxy)propionyl.

2. The compound of claim 1 where X is 2-methyl-2-(2'-nitrophenoxy)propionyl.

3. The compound of claim 1 where R is the optionally protected side chain of an amino acid chosen from the group consisting of glycine, alanine, valine, leucine, isoleucine, threonine, arginine, aspartic acid, phenylalanine, tyrosine, proline, tryptophan and lysine.

4. The compound of claim 3, wherein the optional functional groups present in R are protected by acid-labile protecting groups.

5. The compound of claim 4 wherein said protecting groups are t-alkoxy or t-alkoxycarbonyl groups.

6. The compound of claim 1 wherein R is the optionally protected side chain of an amino acid chosen from the group consisting of glycine, alanine, valine, leucine, isoleucine, threonine, arginine, aspartic acid, phenylalanine, tyrosine, tryptophan and lysine.

7. The compound of claim 1 where X is 2-nitrobenzoyl.

8. The compound of claim 1 where X is 4-chlorobutyryl.

9. The compound of claim 1 where X is acetoacetyl.

10. The compound of claim 1 where X is 4-bromobutyryl.

11. The compound of claim 1 where X is (2-nitrophenoxy)-acetyl.

* * * * *